United States Statutory Invention Registration [19]

[11] Reg. Number: H973

Chaykovsky et al. [43] Published: Oct. 1, 1991

[54] 5-CARBOXYL-1,3-DIAMINO-2,4,6-TRINITROBENZENE AND METHOD OF PREPARATION

[75] Inventors: Michael Chaykovsky, Columbia; Horst G. Adolph, Silver Spring, both of Md.

[73] Assignee: The United States of America as represented by the Secretary of the Navy, Washington, D.C.

[21] Appl. No.: 596,123

[22] Filed: Apr. 2, 1984

[51] Int. Cl.[5] ..... C07C 211/49

[52] U.S. Cl. ..... 558/411; 562/437; 568/933

[58] Field of Search ..... 562/437; 568/933; 558/411

[56] References Cited

U.S. PATENT DOCUMENTS

| | | | |
|---|---|---|---|
| 1,079,246 | 11/1913 | Houben | 562/437 |
| 2,603,659 | 7/1952 | Raasch | 462/437 X |
| 3,314,989 | 4/1967 | Patterson | 562/437 |
| 3,485,865 | 12/1969 | Richter et al. | 562/437 X |
| 3,576,836 | 4/1971 | Prichard | 568/933 X |
| 3,867,452 | 2/1975 | Wilcox | 568/933 X |
| 4,101,721 | 7/1978 | Rich et al. | 562/437 X |
| 4,173,591 | 11/1979 | Koppes et al. | 568/933 |
| 4,399,303 | 8/1983 | Milford, Jr. | 562/437 |

FOREIGN PATENT DOCUMENTS

| | | | |
|---|---|---|---|
| 727657 | 2/1966 | Canada | 562/437 |
| 58924 | 9/1982 | European Pat. Off. | 562/437 |
| 106510 | 12/1898 | Fed. Rep. of Germany | 562/437 |
| 324471 | 2/1935 | Italy | 562/437 |
| 57-26652 | 2/1982 | Japan | 562/437 |

OTHER PUBLICATIONS

Goldstein, et al., "Sur l'acide dinitro-3,5-fluoro-2-benzoique", Helv. Chim. Acta., v. 37, 1954, No. 134, p. 1121.

Ammon et al., "Crystallographic Studies 3,5-diamino 2-4,6-trinitrobenzamide" Acta Cryst. (1982) B38 2083.

*Primary Examiner*—Robert L. Stoll
*Assistant Examiner*—Joseph D. Anthony
*Attorney, Agent, or Firm*—Kenneth E. Walden; Roger D. Johnson

[57] ABSTRACT

5-carboxy-1,3-diamino-2,4,6-trinitrobenzene (DATBA), which is prepared by reacting 5-fluoro-1,3-diamino-2,4,6-trinitrobenzene with cyanotrimethylsilane to form 5-cyano-1,3-diamino-2,4,6-trinitrobenzene which is then hydrolyzed with a strong acid to form the DATBA.

2 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

INPACT SENSITIVITY - DETONATION PRESSURE RELATIONSHIPS

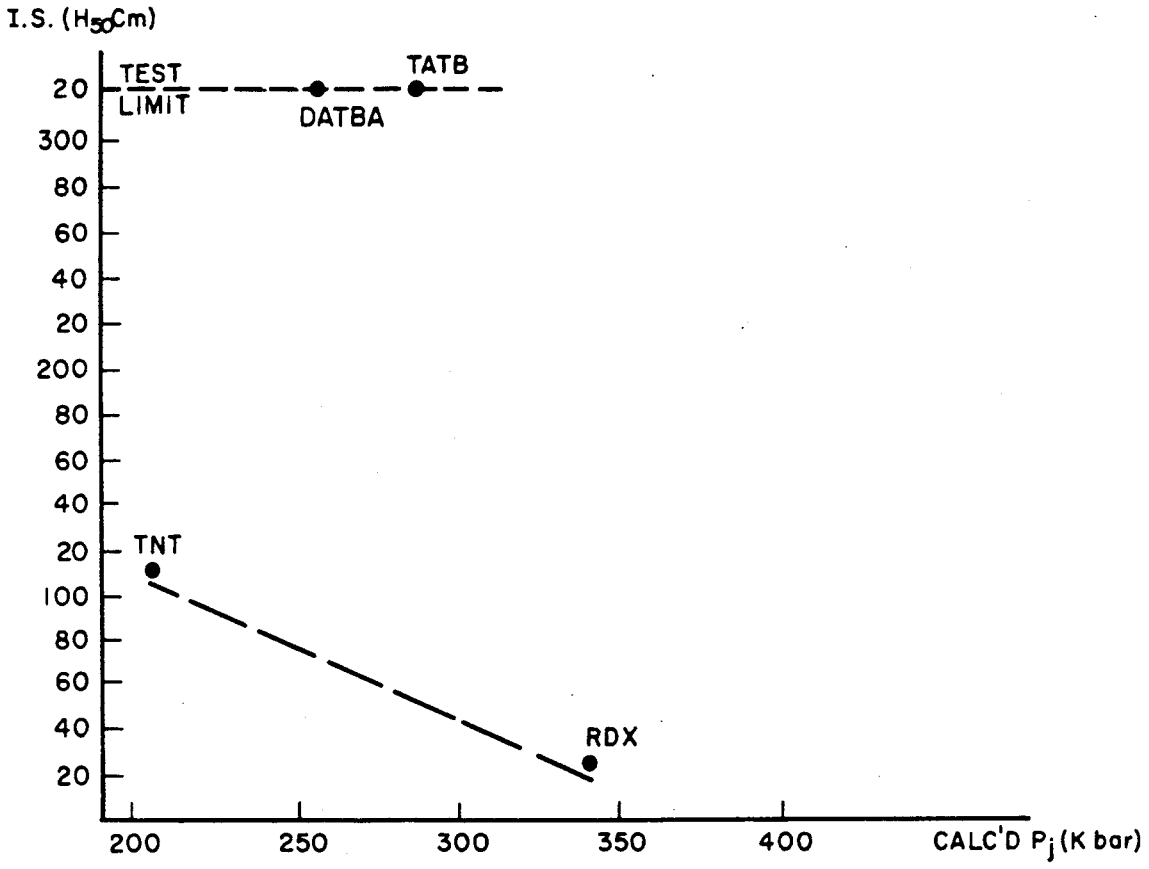
INPACT SENSITIVITY-DETONATION PRESSURE RELATIONSHIPS

5-CARBOXYL-1,3-DIAMINO-2,4,6-TRINITROBENZENE AND METHOD OF PREPARATION

BACKGROUND OF THE INVENTION

This invention generally relates to aromatic nitro compounds and more particularly to 5-carboxy-1,3-diamino-2,4,6-trinitrobenzene and a method of preparation thereof.

Currently used explosive charges contain TNT, RDX, and HMX as the principal ingredients. These compounds are relatively sensitive to impact and other stimuli. Explosive compounds such as 1,3-diamino-2,4,6-trinitrobenzene (DATB) and 1,3,5-triamino-2,4,6-trinitrobenzene (TATB) are less sensitive to impact at comparable performance levels. DATB and TATB are mixed with TNT, RDX, HMX, or mixtures thereof to provide explosives which are less sensitive but which provide comparable detonation pressures.

It would be desirable to provide explosive compositions which are even less sensitive to impact and temperature while still providing high detonation pressures.

SUMMARY OF THE INVENTION

Accordingly, it is an object of this invention to provide a new explosive compound and a method of preparing it.

Another object of this invention is to provide a new explosive having a high energy density.

A further object of this invention is to provide a safer explosive which is less likely to detonate accidently.

These and other objects of this invention are accomplished by providing 5-carboxy-1,3-diamino-2,4,6-trinitrobenzene and a method of preparation thereof. The compound is prepared by reacting 5-fluoro-1,3-diamino-trinitrobenzene with cyanotrimethylsilane to produce 5-cyano-1,3-diamino-2,4,6-trinitrobenzene which is then hydrolyzed to form the desired 5-carboxy-1,3-diamino-2,4,6-trinitrobenzene.

BRIEF DESCRIPTION OF THE DRAWING

A more complete understanding of the invention and the many attendant advantages thereto will be readily appreciated as the same becomes better understood by reference to the following detailed description when considered in connection with the accompanying drawing wherein the impact sensitivity-detonation pressure relationships for 5-carboxy-1,3-diamino-2,4,6-trinitrobenzene (DATBA) and three known explosives (TNT, TATB, and RDX) are plotted.

DETAILED DESCRIPTION OF THE PREFERRED EMBODIMENT

Referring to the FIGURE, 5-carboxy-1,3-diamino-2,4,6-trinitrobenzene (DATBA),

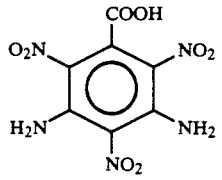

combines a detonation pressure greater than TNT with a high degree of impact insensitivity. Moreover, DATBA offers advantages over other impact insensitive explosives such as 1,3-diamino-2,4,6-trinitrobenzene (DATB) and 1,3,5-triamino-2,4,6-trinitrobenzene (TATB). DATBA should be less sensitive than DATB due to the presence of an additional carboxyl group. Moreover, DATBA is potentially less expensive than TATB if it is made from commercially available 3,5-diaminobenzoic acid. Finally, the decarboxylation step occurring near 240° C.,

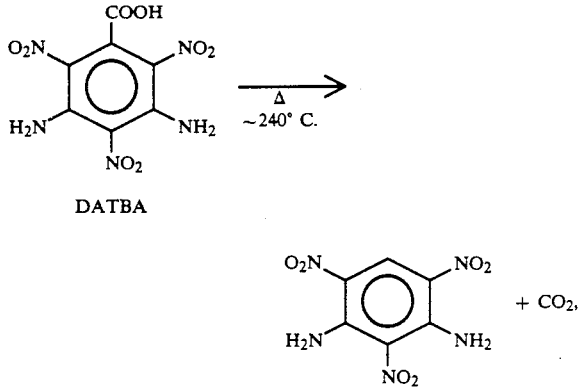

provides an energy sink when DATBA is exposed to elevated temperature and thus should increase its resistance to cookoff and thermal explosion. Therefore, DATBA should be a more effective desensitizing agent than TATB or DATB and should permit the formulation of explosive compositions with improved sensitivity vs. performance characteristics.

In a typical application, DATBA is combined with another explosive filler such as HMX or RDX in the desired ratio and processed into a PBX or Octol type composite under the same conditions used for RDX or HMX alone.

Examples 1 to 2 illustrate a method of preparing the starting material 5-fluoro-1,3-diamino-2,4,6-trinitrobenzene from 1,3,5-trifluorobenzene.

The intermediate compound 5-cyano-1,3-diamino-2,4,6-trinitrobenzene (DATBN) is obtained by the reaction of 5-fluoro-1,3-diamino-2,4,6-trinitrobenzene (F-DATB) with cyanotrimethylsilane,

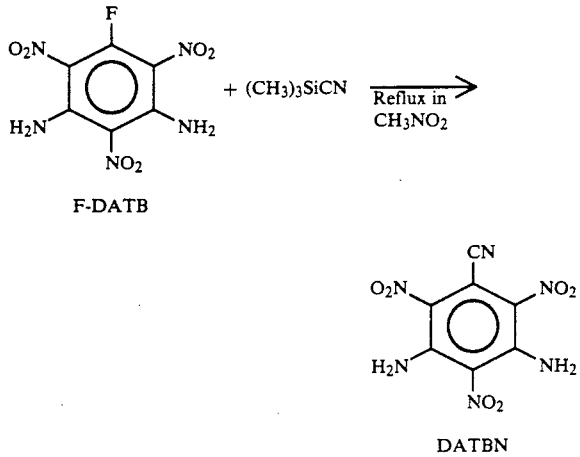

Example 3 illustrates the reaction conditions and a method purification.

In the final step, the DATBN is hydrolyzed with a strong acid to produce the final product 5-carboxy-1,3-diamino-2,4,6-trinitrobenzene (DATBA),

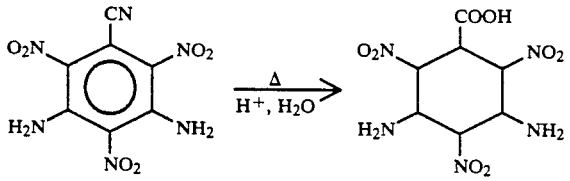

DATBN DATBA

Example 4 illustrates the conditions for this reaction and a method for purifying the final product DATBA.

The general nature of the invention having been set forth, the following examples are presented as specific illustrations thereof. It will be understood that the invention is not limited to these specific examples, but is susceptible to various modifications that will be recognized by one of ordinary skill in the art.

Example 1 is incorporated from U.S. Pat. No. 4,173,591, entitled "Process for the Preparation of 1,3,5-trifloro-2,4,6-trinitrobenzene," which issued on Nov. 6, 1979, to William M. Koppes, Horst G. Adolph, and Michael E. Sitzmann. This example illustrates a method of preparing the 1,3,5-trifluoro-2,4,6-trinitrobenzene starting material.

EXAMPLE 1

1,3,5-trifluoro-2,4,6-trinitrobenzene

Prior Art

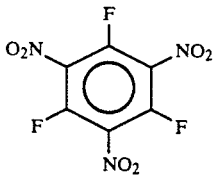

A 3 liter 3-necked Morton flask equipped with Teflon TM paddle stirrer and thermometer and containing 1200 ml of 30% fuming sulfuric acid (8.78 mol $SO_3$) was cooled with an icebath while 280 g (2.76 mol) of $KNO_3$ were added in portions to maintain a temperature not exceeding 50° C. The reaction flask was placed in an oil bath and 1,3,5-trifluorobenzene (56.0 g, 0.424 mol) was added through an addition funnel. The addition rate was controlled to maintain the temperature at about 50° C. The funnel was exchanged for a condenser protected with a drying tube (Drierite) and the mixture was heated at 153°-156° C. for 72 hours. The mixture was allowed to cool to 30° C. and extracted in the reaction flask with $CH_2Cl_2$(3×1200 ml). The combined extracts were concentrated by distillation to 250 ml and this solution treated with $Na_2SO_4$ and filtered. Dry hexane (150 ml) was added to the hot filtrate. After treatment with charcoal the hot solution was filtered. A total of 60.8 g of 1,3,5-trifluoro-2,4,6-trinitrobenzene mp 80°-82° C. (54%) was obtained by concentration of the solution and further addition of hexane. Evaporation of the mother liquor left a 1.4 g residue composed of a 26/74 mixture of 1,3,5-trifluoro-2,4,6-trinitrobenzene and 1,3,5-trifluoro-2,4-dinitrobenzene as determined by gas-liquid phase chromatography.

Example 2 illustrates a method of preparing the 5-fluoro-1,3-diamino-2,4,6-tetranitrobenzene (F-DATB) starting material from 1,3,5-trifluoro-2,4,6-trinitrobenzene.

EXAMPLE 2

5-fluoro-1,3-diamino-2,4,6-trinitrobenzene

Prior Art

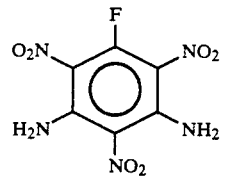

2-amino-2-methylpropane (5.5 g, 75 mmol), in dry dichloromethane (1 500 ml) was added dropwise at 5 ml $min^1$ to a well stirred mixture of 1,3,5-trifluoro-2,4,6-trinitrobenzene (10.0 g, 37.4 mmol), potassium hydrogencarbonate (15.0 g, 150 mmol), and dry dichloromethane (400 ml) at −30° C. under nitrogen. Stirring for 15 hours at room temperature, filtration, and evaporation of the solvent gave a product (14.2 g) which had three components by t.l.c. (benzene solvent). This mixture was stirred for 20 hours in trifluoroacetic acid (50 ml) and dichloromethane (10 ml), and the yellow solid filtered off and extracted with boiling 1,2-dichloromethane (1 600 ml). Filtration gave insoluble 1,3,5-triamino-4,5,6-trinitrobenzene (1.15 g). Concentration of the filtrate to 150 ml gave the desired 5-fluoro-1,3-diamino2,4,6-trinitrobenzene (6.93 g, 70%), m.p. 219°-221° C.

Example 3 illustrates the preparation of the new intermediate compound 5-cyano-1,3-diamino-2,4,6-trinitrobenzene.

EXAMPLE 3

5-Cyano-1,3-diamino-2,4,6-trinitrobenzene

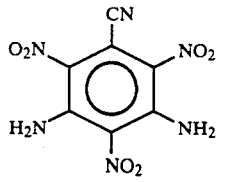

A solution of 5-fluoro-1,3-diamino-2,4,6-trinitrobenzene (F-DATB) (5.22 g, 20 mmol) and cyanotrimethylsilane (4.96 g, 50 mmol) in $CH_3NO_2$ (100 ml) was refluxed for two hours and then evaporated under vacuum to leave a solid residue. Recrystallization from acetonitrile (100 ml) gave 5-cyano-1,3-diamino-2,4,6-trinitrobenzene (4.4 g, 82%) as orange-brown crystals: mp 212°-217° C. dec. An additional recrystallization gave the analytical sample: mp 220°-221° C.; mass spectrum (CI, $CH_4$) m/z 269 (M+1, 100).

Anal. calcd for $C_7H_4N_6O_6$: C, 31.35; H, 1.50; N, 31.34.

Found: C, 31.39; H, 1.74; N, 31.19.

Example 4 illustrates the hydrolysis of 5-cyano-1,3-diamino-2,4,6-trinitrobenzene to form the final produce 5-carboxy-1,3-diamino-2,4,6-trinitrobenzene.

EXAMPLE 4

5-Carboxy-1,3-diamino-2,4,6-trinitrobenzene

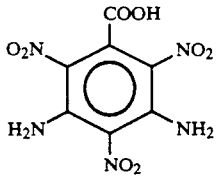

A solution of 5-cyano-1,3-diamino-2,4,6-trinitrobenzene (1.34 g, 5 mmol) in sulfuric acid (30 ml) and $H_2O$ (15 ml) was heated at 100° C. for 90 minutes, cooled, and then poured onto a mixture of ice and $H_2O$ (250 ml). The solid was filtered, washed with $H_2O$, and dried to give 5-carboxy-1,3-diamino-2,4,6-trinitrobenzene (1.33 g, 92.7%). Recrystallization from acetonitrile gave yellow needles: mp 240°–245° C. (loss of $CO_2$) and 280°–282° C. dec: mass spectrum (EI, $CH_4$) m/z 244 ($M+1-CO_2$, 100), 272 ($m+C_2H_5-CO_2$, 9.2), 284 ($M+C_3H_5-CO_2$, 4.5).

Anal. Calcd for $C_7H_5N_5O_8$: C, 29.28; H, 1.76; N, 24.39.

Found: C, 29.33: H, 1.84; N, 24.16.

Obviously, numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. 5-carboxy-1,3-diamino-2,4,6-trinitrobenzene,

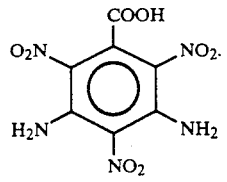

2. 5-cyano-1,3-diamino-2,4,6-trinitrobenzene,

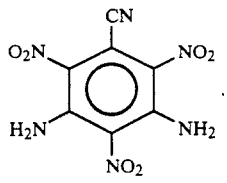

* * * * *